United States Patent [19]

Beschke et al.

[11] 4,139,536

[45] Feb. 13, 1979

[54] PROCESS FOR THE RECOVERY OF NICOTINAMIDE

[75] Inventors: Helmut Beschke; Heinz Friedrich, both of Hanau; Klaus-Peter Müller, Bergheim; Gerd Schreyer, Hanau, all of Fed. Rep. of Germany

[73] Assignee: Deutsche Gold- Und Silber-Scheideanstalt vormals Roessler, Frankfurt, Fed. Rep. of Germany

[21] Appl. No.: 676,197

[22] Filed: Apr. 12, 1976

[30] Foreign Application Priority Data

Apr. 17, 1975 [DE] Fed. Rep. of Germany ....... 2517053

[51] Int. Cl.$^2$ .......................................... C07D 213/56
[52] U.S. Cl. .................................................. 546/317
[58] Field of Search ................. 260/295.5 A, 295 AM

[56] References Cited

U.S. PATENT DOCUMENTS

| 2,471,518 | 5/1949 | Duesel et al. ................. 260/295.5 A |
| 2,904,552 | 9/1959 | Gasson et al. ................ 260/295 AM |

OTHER PUBLICATIONS

Duesel et al., Chem. Abstracts, vol. 43, (19), pp. 7513-i--7514-a; Oct. 10, 1949.
Chem. Abstracts, vol. 40, (9), pp. 2473-2474, under *Nicotinic Acid Amide*, May 10, 1946.
Klingsberg, Pyridine and Its Derivatives, Part Three, Interscience, Pub. pp. 218-219, 1962.

*Primary Examiner*—Alan L. Rotman
*Attorney, Agent, or Firm*—Cushman, Darby & Cushman

[57] ABSTRACT

Nicotinamide is recovered from the reaction mixture resulting from the hydrolysis of nicotinonitrile at elevated temperature by converting the nicotinamide into a melt while removing the solvent.

12 Claims, No Drawings

PROCESS FOR THE RECOVERY OF NICOTINAMIDE

The invention is directed to a process for the recovery of nicotinamide from the reaction mixture resulting from the hydrolysis of nicotinonitrile.

Several processes are known for the production of nicotinamide by the hydrolysis of nicotinonitrile. The use of acid or alkaline acting materials is known. As an acid substance there is used, for example, sulfuric acid (Helv. Chim. Acta Vol. 26 (1943), 361), as alkaline materials there can be used alkaline earth metal oxides or carbonates (British Pat. No. 777,517), alkaline ion exchangers (J.Am. Chem. Soc. Vol. 70 (1948), 3945), manganese dioxide (German Auslegeschrift 2,131,813), sodium hydroxide in admixture with hydrogen peroxide (German Pat. No. 828,247), as well as sodium hydroxide, ammonia or alkaline acting salts (U.S. Pat. No. 2,471,518). In these processes the nicotinamide is recovered while the reaction mixture, in a given case using reducing pressure is evaporated to dryness. This recovery of nicotinamide is expensive, especially on an industrial scale, since it requires large plants. The entire disclosures of the above-mentioned articles, British Pat. No. 777,517, German Auslegeschrift No. 2,131,813, German Pat. No. 828,247 and U.S. Pat. No. 2,471,518 are hereby incorporated by reference and relied upon.

There has now been found a process for the recovery of nicotinamide from the reaction mixture resulting from the hydrolysis of nicotinonitrile by removal of the solvent from the reaction mixture at elevated temperature and separation of the nicotinamide as a solid that is characterized by converting the nicotinamide into a melt while removing of the solvent.

This process is substantially simpler to operate than the known processes. Surprisingly, the formation of byproducts does not occur to a mentionable extent although relatively high temperatures are present in the melt condition.

According to the process of the invention, the nicotinamide can be recovered from the reaction mixture obtained in the customary hydrolysis of nicotinonitrile to nicotinamide, for example, from the reaction mixtures formed in the process of German Pat. No. 828,247 or U.S. Pat. No. 2,471,518.

The process of the invention is used with special advantage if the hydrolysis (according to the process of our simultaneously filed application corresponding to German application P 2517054.1) is carried out by means of aqueous alkali hydroxide, e.g., sodium hydroxide or potassium hydroxide at temperatures between about 110 to 250° C., preferably 120 to 200° C., most preferably 135 to 200° C. There is preferably employed in such hydrolysis 0.3 to 3.0 mole of alkali metal hydroxide per 100 mole of nicotinonitrile. The entire disclosure of our said companion application filed on even date and corresponding to German application P 2517054.1 is hereby incorporated by reference and relied upon.

In the case of employing the hydrolysis reaction mixture of our companion application filed on even date the reaction mixture is in effect free from byproducts except nicotinic acid. Since in the process of the present invention removal of the water from the reaction mixture forms in effect no byproducts there results a nicotinamide of outstanding quality. It can be generally used directly. If an amide exceptionally free of nicotinic acid is needed, for example, for pharmaceutical purposes, the further purification can take place by simple recrystallisation.

According to the present invention, the process of removal of the solvent from the reaction mixture resulting from the hydrolysis is carried out in such manner that the nicotinamide is obtained as a melt. The hydrolysis reaction mixture for this purpose is brought in suitable manner to a temperature above 130° C., preferably to temperatures between about 140 to 200° C., especially 150 to 180° C. If necessary, the operation is carried out under reduced pressure, e.g., at a pressure of 0,005 to 1 bar, especially 0.01 to 0,1 bar.

There can be used the usual apparatuses for removal of solvents from solutions or suspensions in order to carry out the process of the invention. Apparatuses which are suited for a continuous operation and in which the reaction mixture or the melt forming of nicotinamide are heated for only a short time, as for example, thin layer evaporators, or evaporators with rotating installations, are advantageous. Falling film evaporators are especially suitable. According to the solvent content of the reaction mixture, if necessary, several of these apparatuses are connected in succession.

A preferred method of operation is to use several falling film evaporators and to continuously operate these connected in succession so that from the next to last evaporator there is produced a melt having a solvent content of about 1 to 5 weight % and from the last evaporator a melt with a solvent content of less than 0.5 weight %.

This process is especially recommended with the reaction mixture resulting from the hydrolysis of the nitrile by means of aqueous alkali hydroxide solutions at temperatures between about 110 to 250° C. and which solutions generally contain 30 to 70 weight %, especially about 40 to 60 weight % of water. Advantageously two falling film evaporators are employed and the reaction mixture resulting from the hydrolysis is continuously directly fed thereto. Suitably the first of the two evaporators connected in series is held at normal pressure and the second is operated below 0.2 bar while the temperature in the evaporators is held between about 150 to 180° C.

The melt of nicotinamide resulting from the removal of the solvent solidifies during the cooling down as crystals. It is advantageous to bring the melt onto a cooled surface on which the melt can be slowly cooled in a thin layer. There can be used the usual apparatus employed for this purpose.

It is particularly favorable, namely, with a continuous accumulation of the melt to use a cooling belt. The melt is advantageously cooled slowly on this belt, first by cooling the belt with air, then by cooling the belt with water and, if necessary, finally by cooling the belt with cooling brine.

In a given case it is advantageous to bring the melt to solidification in an inert organic liquid. The solidified product can be comminuted directly in a conventional apparatus for this purpose, if necessary, adding a grinding aid. For example, suitable apparatus include roller breakers, hammer mills, spiked mills or blast mills.

The nicotinamide obtained from the melt can, if necessary, be freed from impurities in customary manner, for example by recrystallization. Insofar as there is employed a nicotinamide which is formed by hydrolysis of the nitrile by means of aqueous alkali hydroxide at temperatures between about 110 and 250° C., the product is suited for most purposes without purification, for example, for use as a fodder additive. However, in case the nicotinamide recovered should be completely free of nicotinic acid, for example for pharmaceutical purposes, the melt is introduced with stirring into a liquid which is a selective solvent for the nicotinamide, and the nicotinamide is precipitated from this liquid. As liquids there are suited ketones, alcohols, and esters, especially acetone, methyl ethyl ketone, propanol-2, butanol-2, 2-methylpropanol-1 and ethyl acetate.

Unless otherwise indicated all parts and percentages are by weight.

EXAMPLE 1

There was used a 9 meter long flow tube filled with packing of wire screens and a free diameter of 25 mm. There was an inlet pipe for the nicotinonitrile solution at the beginning of the tube and three inlet pipes for the alkali hydroxide solution, one being at the beginning of the tube, the second after 3 meters and the third after 6 meters of the length of the tube. There was fed in a uniform stream hourly a solution of 10.0 kg of nicotinonitrile in 13.5 kg of water heated to 130° C. Besides, there was added a 10% aqueous sodium hydroxide solution, namely, from this solution there was led hourly in uniform flow 113 grams at the beginning of the tube, 225 grams after 3 meters, and 415 grams after 6 meters of the tube length. The tube was held at 130° C. over the entire length by heating or cooling. The pressure in the tube was 4 bar.

The hydrolysis mixture which was drawn off from the tube at the end had a pH value of 8.0. It was led directly into a falling films evaporator having a diameter of 40 mm and a length of 3 meters, which was heated with steam at a pressure of 9 bar to 170° C. The melt of nicotinamide which was delivered from this evaporator contained 2.4 weight % of water. It was led to a second falling film evaporator which was heated to 170° C. and operated at a pressure of 0.03 bar. The melt which was recovered from this evaporator had a water content of 0.2 weight %. There was accumulated in the falling film evaporators as distillate an aqueous solution which hourly contained 0.4 kg of nicotinotrile. From the second falling film evaporator the melt was directly led to a steel cooling belt having a length of 4 meters and a width of 0.3 meters. The cooling belt, that had a speed of 0.15 meters per second was not cooled in the first third and was water cooled in the following two thirds.

The product cooled on the belt was comminuted with a breaker and ground with a spike mill. The yield was 11.3 kg per hour. The product consisted of 97.2 weight % nicotinamide and also contained 2.4 weight % sodium nicotinate, 0.05 weight % nicotinonitrile and 0.25 weight % water. The product was suitable directly for use as a fodder additive.

EXAMPLE 2

The process was the same as in Example 1 but the melt was not led out of the second falling film evaporator to a cooling belt but was introduced with stirring into 2-methyl-propanol-1. There were added hourly 21.7 kg of 2-methyl-propanol-1 which was held at the boiling point. The mixture was filtered hot. There remained 500 grams of filter residue per hour, which residue was essentially sodium nicotinate. There was separated from the filtrate by cooling to 5° C. the nicotinamide, namely, 9.6 kg per hour was recovered. The nicotinamide had the purity necessary for pharmaceutical purposes. In evaporation of the mother liquod there were accumulated 1.1 kg of nicotinamide contaminated with sodium nicotinate. By recrystallization there was recovered from this 0.8 kg of pure nicotinamide.

The process can comprise, consist essentially of or consist of the steps set forth with the materials recited.

What is claimed is:

1. A process for the recovery of nicotinamide from the reaction mixture resulting from the aqueous hydrolysis of nicotinonitrile at elevated temperature comprising converting the nicotinamide into a melt while removing the solvent at a temperature above 130° C.

2. The process of claim 1 including the step of directly cooling the melt to form solid nicotinamide.

3. The process of claim 1 wherein the reaction mixture employ is one obtained by hydrolysis with alkali metal hydroxide at 110 to 250° C.

4. The process of claim 1 wherein the solvent is removed at a temperature between 130° C. and 200° C.

5. The process of claim 4 wherein the solvent is removed at 140 to 200° C.

6. The process of claim 5 wherein the solvent is removed at 150 to 180° C.

7. The process of claim 4 wherein the solvent at least in the final stages is removed at reduced pressure.

8. The process of claim 7 wherein the terminal pressure for removal of the solvent is below 0.2 bar.

9. The process of claim 4 wherein the solvent is removed in a plurality of steps which the last step being carried out at a pressure of below 0.2 bar.

10. The process of claim 9 wherein the melt prior to the last solvent removal step has a solvent content of about 1 to 5 weight % and the last step of solvent removal is continued until the solvent content is below 0.5 weight %.

11. The process of claim 4 wherein the solvent removal is carried out at least in part in a falling film evaporator.

12. The process of claim 4 wherein the solvent is removed from the melt until the melt has a solvent content of below 0.5%.

* * * * *